United States Patent
Shah et al.

(10) Patent No.: US 11,141,414 B2
(45) Date of Patent: Oct. 12, 2021

(54) PHARMACEUTICAL COMPOSITIONS COMPRISING A PH-DEPENDENT COMPONENT AND PH-RAISING AGENT

(71) Applicant: OHEMO LIFE SCIENCES INC., Juncos, PR (US)

(72) Inventors: Manish S. Shah, West Caldwell, NJ (US); Ray J. DiFalco, Ridgewood, NJ (US)

(73) Assignee: Ohemo Life Sciences, Inc., Juncos, PR (US)

( * ) Notice: Subject to any disclaimer, the term of this patent is extended or adjusted under 35 U.S.C. 154(b) by 0 days.

(21) Appl. No.: 14/498,865

(22) Filed: Sep. 26, 2014

(65) Prior Publication Data

US 2015/0017240 A1    Jan. 15, 2015

Related U.S. Application Data

(63) Continuation of application No. PCT/US2014/029917, filed on Mar. 15, 2014.

(60) Provisional application No. 61/799,031, filed on Mar. 15, 2013.

(51) Int. Cl.
| | |
|---|---|
| *A61K 31/485* | (2006.01) |
| *A61K 9/20* | (2006.01) |
| *A61K 47/02* | (2006.01) |
| *A61K 9/28* | (2006.01) |
| *A61K 47/30* | (2006.01) |

(52) U.S. Cl.
CPC .......... *A61K 31/485* (2013.01); *A61K 9/2009* (2013.01); *A61K 9/2022* (2013.01); *A61K 9/2813* (2013.01); *A61K 47/02* (2013.01); *A61K 47/30* (2013.01)

(58) Field of Classification Search
None
See application file for complete search history.

(56) References Cited

U.S. PATENT DOCUMENTS

| | | | |
|---|---|---|---|
| 8,394,409 B2 | 3/2013 | Odidi et al. | |
| 8,637,540 B2 | 1/2014 | Kumar et al. | |
| 8,822,489 B2 | 9/2014 | Kumar et al. | |
| 2003/0170181 A1 | 9/2003 | Midha | |
| 2004/0006072 A1 | 1/2004 | Franz et al. | |
| 2004/0234608 A1 | 11/2004 | Fleshner-Barak et al. | |
| 2005/0220878 A1* | 10/2005 | Fegely | A61K 9/286 424/473 |
| 2005/0232987 A1 | 10/2005 | Srinivasan et al. | |
| 2006/0229226 A1 | 10/2006 | Giniger et al. | |
| 2007/0231268 A1 | 10/2007 | Emigh et al. | |
| 2008/0102121 A1 | 5/2008 | Devane et al. | |
| 2008/0113025 A1 | 5/2008 | Devane et al. | |
| 2008/0206332 A1 | 8/2008 | Kidney et al. | |
| 2008/0311197 A1 | 12/2008 | Arkenau-Maric et al. | |
| 2008/0311205 A1 | 12/2008 | Habib et al. | |
| 2009/0028873 A1 | 1/2009 | Gant et al. | |
| 2010/0216829 A2 | 8/2010 | Kumar et al. | |
| 2011/0076325 A1 | 3/2011 | Shah et al. | |
| 2011/0077238 A1 | 3/2011 | Leech et al. | |
| 2012/0009129 A1 | 1/2012 | Brzeczko | |
| 2012/0202838 A1 | 8/2012 | Ghosh et al. | |
| 2012/0202839 A1* | 8/2012 | Emigh | A61K 9/0043 514/282 |
| 2013/0005823 A1 | 1/2013 | Emigh et al. | |
| 2013/0095176 A1 | 4/2013 | Odidi et al. | |
| 2013/0171257 A1 | 7/2013 | Kumar et al. | |
| 2014/0010860 A1 | 1/2014 | Odidi et al. | |
| 2014/0155388 A1* | 6/2014 | Brzeczko et al. | 514/220 |

FOREIGN PATENT DOCUMENTS

| | | |
|---|---|---|
| WO | WO 2002/100382 A2 | 12/2002 |
| WO | WO 2006/058249 A2 | 6/2006 |
| WO | WO 2009/023672 A2 | 2/2009 |
| WO | WO 2011/066980 A2 | 6/2011 |
| WO | WO 2011066980 A2 * | 6/2011 |

OTHER PUBLICATIONS

European Search Report for EP 14764019.7 dated Jun. 22, 2016.

* cited by examiner

*Primary Examiner* — H. Sarah Park
(74) *Attorney, Agent, or Firm* — William Beaumont; Juneau & Mitchell

(57) ABSTRACT

An oral pharmaceutical composition in unit dosage form comprising: (1) a first portion comprising: an active ingredient and a pH-dependent component, and (2) a second portion comprising a pH-raising agent is provided. Methods of administering the composition are also provided.

14 Claims, No Drawings

PHARMACEUTICAL COMPOSITIONS COMPRISING A PH-DEPENDENT COMPONENT AND PH-RAISING AGENT

CROSS-REFERENCE TO RELATED APPLICATION

This application is a continuation of PCT International Application No. PCT/US14/29917, filed on Mar. 15, 2014, which claims priority to U.S. Provisional Patent Application No. 61/799,031, filed on Mar. 15, 2013, the disclosure of each of which is hereby incorporated in its entirety by reference.

FIELD OF THE INVENTION

The present invention provides abuse resistant pharmaceutical compositions, methods of administration, and methods of making the same.

BACKGROUND OF THE INVENTION

The present invention relates to orally administrable pharmaceutical compositions, and specifically relates to compositions that are designed to reduce the potential for improper administration of medications and their use in a non-indicated or non-prescribed manner. The present invention can comprise any active ingredient, and it is especially useful with medications that are subject to abuse, such as drugs affecting the central nervous system. For example, the present invention is particularly useful for pain medications, medications to reduce or eliminate anxiety attack (psychotherapeutic drugs), stimulants and sleeping pills. With these general types of drugs, there is the potential of abuse that may result in drug overdose, addiction, suboptimal efficacy, and/or death.

Opioid agonists are substances that act by attaching to specific proteins called opioid receptors, which are found in the brain, spinal cord, and gastrointestinal tract. When these drugs attach to certain opioid receptors in the brain and spinal cord they can effectively block the transmission of pain messages to the brain. Opioid analgesics such as oxycodone, morphine, oxymorphone, hydrocodone and hydromorphone are successful and therapeutically useful pain medications. Unfortunately, they also pose a severe threat for willful abuse due to their ability to alter mood and/or cause a sense of euphoria (a "high").

When administered properly, at recommended doses, pharmaceutical compositions comprising drugs can be safe and effective and provide an adequate and effective amount of drug. Individuals taking the recommended or prescribed quantity of drug can achieve the intended therapeutic effect, such as pain relief. However, taking a higher than recommended quantity of dosage units can sometimes result in a high serum concentration of drug, which can lead to a "high" or sense of euphoria. Therefore, some individuals, in an attempt to achieve this "high," administer more than the recommended quantity of dosage units, or they place a large number of units in a liquid, such as in a glass of water, and either swallow or inject the drug. For example, in some cases, it may be recommended or prescribed to administer one or two tablets to treat a condition such as pain. However, an abuser may take three or more tablets at one time or within a short period of time in order to achieve an amplified effect or "high."

It is an object of the present invention to provide an orally administrable pharmaceutical composition that significantly reduces the potential for improper administration or use of drugs while, when administered as directed, is capable of delivering a therapeutically effective dose. In particular, the present invention addresses the need for a drug product which, compared to conventional formulations, decreases the intensity, quality, frequency and rate of occurrence of the euphoria effect that can occur with improper administration.

SUMMARY OF THE INVENTION

The present invention provides an oral pharmaceutical composition in unit dosage form comprising: (1) a first portion comprising: an active ingredient and a pH-dependent component, and (2) a second portion comprising a pH-raising agent.

The present invention also provides a method of making an oral pharmaceutical composition in unit dosage form comprising: forming a first portion comprising: an active ingredient and a pH-dependent component, and applying thereto a second portion comprising a pH-raising agent.

The present invention also provides a method of treating a condition comprising administering to a subject in need thereof the pharmaceutical composition of the present invention.

DETAILED DESCRIPTION OF THE INVENTION

The present invention provides an abuse resistant oral pharmaceutical composition in unit dosage form which, when administered appropriately, can provide a therapeutic amount of an active ingredient to a subject to accomplish a pharmaceutical effect, such as pain relief, while minimizing the ability of a potential abuser to experience a "high" through improper administration of the composition. When administered as directed, the pharmaceutical composition may provide an effective amount of an active ingredient to a subject. However, when a higher than recommended or prescribed number of unit dosage forms is administered, for example in an attempt to experience a "high," then the release of the active ingredient from the dosage form may be retarded or reduced, e.g., in the stomach.

The present invention provides an oral pharmaceutical composition in unit dosage form comprising: (1) a first portion comprising: an active ingredient and a pH-dependent component, and (2) a second portion comprising a pH-raising agent. The term "unit dosage form" refers to physically discrete units suitable as unitary dosages for administration to a subject. Examples of unit dosage forms include but are not limited to tablets and capsules. In preferred embodiments, the unit dosage form comprises a tablet.

The term "first portion" refers to a portion of the pharmaceutical composition containing an active ingredient and a pH-dependent component. The first portion may comprises one or more active ingredients. The term "active ingredient" includes any compound or drug which has pharmacological, therapeutic, or biological activity. In some embodiments, the active ingredient include, but are not limited to analgesics, anti-inflammatory agents, anti-helminthics, anti-arrhythmic agents, anti-asthma agents, anti-bacterial agents, anti-viral agents, anti-coagulants, anti-dementia agents, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, immunosuppressants, anti-protozoal agents, anti-thyroid agents, anti-tussives, anxiolytics, sedatives, hypnotics, neuroleptics, neuroprotective agents, β-blockers, cardic inotropic agents, cell adhesion inhibitors, corticosteroids, cytokine receptor activity modulators, diuretics, anti-Parkinson's agents, gastro-intestinal agents, histamine H-receptor antagonists, keratolytics, lipid regulating agents, muscle relaxants, nitrates and other anti-anginal agents, non-steroid anti-asthma agents, nutritional agents, opioid analgesics, sex hormones, stimulants and anti-erectile dysfunction agents; and salts, esters, and mixtures thereof. In preferred embodiments, the active ingredient comprises a drug which is often abused, such as central nervous system stimulants and depressants. Examples of central nervous system stimulants include, but are not limited to, amphetamines and agents such as cocaine. Examples of central nervous depressants include, but are not limited to but are not limited to opioids, barbiturates, benzodiazepines, and other anxiety and sleep medications.

Stimulants increase heart rate, blood pressure and metabolism, sometimes providing feelings of exhilaration and energy and increased mental alertness. Amphetamines such as methylphenidate (sometimes marketed under the tradename RITALIN®) dextroamphetamine (sometimes marketed under the tradenames ADDERALL® and DEXEDRINE®), modafinil (PROVIGIL®), and dexmethylphenidate (FOCALIN®) are often prescribed for the treatment of narcolepsy, attention-deficit/hyperactivity disorder, and depression that has not responded to other treatments. They also may be used for short-term treatment of obesity. Individuals may become addicted to the sense of well-being and enhanced energy that stimulants can generate. Taking high doses of stimulants repeatedly over a short time, however, can lead to feelings of hostility or paranoia. Additionally, taking high doses of stimulants may result in dangerously high body temperatures and an irregular heartbeat.

Examples of opioids include, but are not limited to the following: alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, and tramadol. Any opioid or pharmaceutically acceptable salt or ester thereof may be used in the abuse deterrent composition. Preferred opioids include fentanyl, sufentanil, carfentanil, lofentanil, alfentanil, hydromorphone, oxycodone, morphine, hydroxycodone, propoxyphene, pentazocine, methadone, tilidine, butorphanol, buprenorphine, levorphanol, codeine, oxymorphone, meperidine, and dihydrocodeinone. More preferred opioids include oxycodone, hydrocodone, codeine, morphine, oxymorphone and hydromorphone, and pharmaceutically acceptable salts and esters thereof. The most particularly preferred opioids are oxycodone and morphine and pharmaceutically acceptable salts thereof.

Examples of barbiturates include, but are not limited to mephobarbital (which is sometimes marketed under the tradename MEBARAL®) and pentobarbital sodium (which is sometimes marketed under the tradename NEMBUTAL®). Barbiturates are often prescribed to treat anxiety, tension, and sleep disorders.

Examples of benzodiazepines and benzodiazepine derivatives include, but are not limited to diazepam (sometimes marketed under the tradename Valium®), alprazolam (sometimes marketed under the tradename Xanax®), triazolam (Halcion®), and estazolam (ProSom®). Other example include: chlordiazepoxide, temazepam, lorazepam, clonazepam, flurazepam, midazolam, and oxazepam. Benzodiazepines are often prescribed to treat anxiety, acute stress reactions, and panic attacks.

An example of another CNS depressant is zaleplon, which is sometimes marked under the tradename SONATA®.

Preferred embodiments of the invention include an active ingredient in the amounts as follows: oxycodone or a pharmaceutically acceptable salt thereof, which is present in an amount of about 3 mg to about 400 mg; morphine or a pharmaceutically acceptable salt thereof, which is present in an amount of about 5 mg to about 800 mg; hydromorphone or a pharmaceutically acceptable salt thereof, which is present in an amount of about 1 mg to about 64 mg; hydrocodone or a pharmaceutically acceptable salt thereof, which is present in an amount of about 5 mg to about 400 mg; and oxymorphone or a pharmaceutically acceptable salt thereof, which is present in an amount of about 4 mg to about 80 mg.

The term "pH-dependent component" refers to a part of the first portion which may be affected by the pH of the surrounding environment. In particular, the pH-dependent component may comprise a compound, such as a polymer, whose characteristics, such as chemical and/or physical properties, vary according to the pH of the surrounding environment. The surrounding environment may comprise any type of liquid medium, such as gastric fluid. In some embodiments wherein the pharmaceutical composition is orally administered, the surrounding liquid may comprise gastric fluid. In some other embodiments, the surrounding liquid may be the liquid in which the pharmaceutical composition is placed, such as water, an acidic or alkaline solution. The pH-dependent component may comprise acid sensitive material. In some embodiments, the pH-dependent component is affected by (i.e., dissolves when exposed to) a decrease in pH. In some embodiments, the pH-dependent component is affected when the pH is below about 6, preferably below 5, more preferably below 4, and even more preferably below 3. In some embodiments, the characteristics of the pH-dependent component may be affected to a greater degree at different pHs. For example, the pH-dependent component's physical or chemical characteristics may be affected to a greater degree at a pH of 4 or lower, compared to at a pH of 5.

The pH-dependent component may comprise a compound such as a pharmaceutical excipient. In some embodiments, the pH-dependent component comprises a pH-dependent polymer. Examples of pH-dependent polymers include, but are not limited to certain methacrylate-based polymers, such as cationic polymers with a dimethylaminoethyl ammonium group. These polymers are marketed under trade names such as EUDRAGIT® E 100 and EUDRAGIT® E PO.

In some embodiments wherein the pH-dependent component comprises a pH-dependent polymer, the polymer may dissolve when there is a decrease in pH. In some embodiments, wherein the pH-dependent polymer comprises a matrix containing the active ingredient, a decrease in pH may result in the dissolution of the polymer and release of the active ingredient.

In some embodiments, the pH-dependent component may form a part or section of the first portion which is separate from the part or section of the first portion comprising the active ingredient. In some embodiments, the pH-dependent component may be comprise coating, and the coating may partially or substantially cover the part within the first portion comprising the active ingredient, wherein the active ingredient-containing part could be, for example, a tablet core or layer or a capsule. The term "substantially cover" means that preferably more than 70%, more preferably more than 80%, even more preferably more than 90%, and most preferably more than 95% of the part of the first portion comprising the active ingredient is covered by the pH-dependent component. In some embodiments, 100% coverage is suitable.

In some other embodiments, the pH-dependent component may comprise the active ingredient and does not form a separate section within the first portion. For example, the pH-dependent component may comprise particles of the active ingredient which are distributed within the pH-dependent component. In some embodiments, the pH-dependent component may comprise a matrix and further comprise active ingredient within the matrix.

The term "second portion" refers to the portion of the pharmaceutical composition which comprises a permeability increasing agent or a pH-raising agent. The term "permeability agent" refers to any agent which can enhance the permeability of the second portion, such as a surfactant. An example of a surfactant includes, but it not limited to sodium lauryl sulfate. The term "pH-raising agent" includes any agent which has the ability to increase the pH of a liquid. Examples of pH-raising agents include, but are not limited to alkalinizing agents such as antacid compounds and acid inhibitors or reducers such as histamine-2 receptor antagonists and proton pump inhibitors. Examples of alkalinizing agents include, but are not limited to, carbonate and bicarbonate-containing compounds such as sodium bicarbonate, potassium bicarbonate and calcium carbonate; and hydroxide-containing compounds such as aluminum hydroxide and magnesium hydroxide. Examples of histamine-2 receptor antagonists include, but are not limited to ranitidine, famotidine, nizatidine, and cimetidine. Examples of proton pump inhibitors include, but are not limited to omeprazole, esomeprazole, pantoprazole, lansoprazole, dexlansoprazole, and rabeprazole. In preferred embodiments, the pH-raising agent comprises an alkalinizing agent, preferably calcium carbonate or sodium bicarbonate.

The amount of pH-raising agent present in the second portion is an amount sufficient to raise the pH of the gastric fluid or surrounding liquid to inhibit release of the active ingredient when a plurality of unit dosage forms are administered or placed in the liquid. In some embodiments, the amount of pH-raising agent present in the second portion is an amount sufficient to raise the pH of gastric fluid after administration to a subject of two or more unit dosage forms. In some embodiments, the second portion may be formulated to contain an amount of pH-raising agent which raises the pH when at least a designated number of unit dosage forms is administered concurrently or within a short time period, for example, within one hour, preferably 30 minutes, more preferably 15 minutes, and most preferably within 5 minutes. For example, the second portion may comprise a pH-raising agent in an amount that is sufficient to increase the pH of the surrounding liquid, when two or more unit dosage forms are administered concurrently or within a time period, for example, within one hour, preferably 30 minutes, more preferably 15 minutes, and most preferably within 5 minutes. In some embodiments, the greater the number of unit dosage forms administered, the greater the increase in pH of the surrounding liquid.

In embodiments wherein the pH-raising agent is an alkalinizing agent, such as aluminum hydroxide, magnesium hydroxide, sodium bicarbonate, potassium bicarbonate, or calcium carbonate, the amount of the alkalinizing agent is present in the second portion in an amount of about 10 mg to about 5,000 mg, preferably about 50 mg to about 2,500 mg, more preferably about 100 mg to about 2,000 mg, even more preferably about 250 mg to about 1,500 mg, and most preferably about 500 mg to about 1,000 mg.

In some embodiments, part or all or the first portion may be in direct physical contact with part or all of the second portion. A part is in "direct physical contact" with another part when the parts are directly adjacent to each other in the pharmaceutical composition without intervening or intermediate portions. In some embodiments, the first portion and second portion are not in direct physical contact with each other, and no part of the first portion is in direct physical contact with the second portion in the pharmaceutical composition. For example, a further portion, such as one or more intermediate layers, may be present between the first portion and the second portion.

In some embodiments wherein the first portion is in direct physical contact with the second portion, substantially all or all of the entire surface area of the first portion may be in contact with the second portion, such as when the first portion comprises an first layer of core which is substantially or completely surrounded by the second portion (for example, a layer or coating), or when there are multiple first portion sections which are distributed within the second portion. In some embodiments, only part of the surface area (less than the entire surface area) of the first portion and the second portion are in contact with each other in the composition.

In some embodiments, the second portion at least partially covers the first portion, and preferably, the second portion substantially covers the first portion. Substantial covering of the first portion occurs when more than 70%, more preferably more than 80%, even more preferably more than 90%, and most preferably more than 95% of the first portion is covered by the second portion. In some embodiments, 100% coverage is suitable. The second portion is preferably contiguous and may comprise one or more layers, coatings, or other contiguous sections. In some embodiments, the first portion comprises a core, and the second portion comprises a layer or coating surrounding the core. In some other embodiments, the first portion and second portion are each layers in a bilayer or multilayer tablet, for example. In some other embodiments, the first portion is present inside a capsule shell, and the second portion comprises a coating on the capsule shell.

The combination of the pH-dependent component and pH-raising agent may contribute to the abuse deterrent aspect of the pharmaceutical composition. When the pharmaceutical composition is administered or placed in a liquid, and the pH of the surrounding liquid reaches or exceeds a particular pH, then the pH-dependent component may contribute to inhibiting the release of the active ingredient in the first portion. In some embodiments, when a higher than necessary or recommended number of unit dosage forms is administered or placed in a liquid (for example, in an attempt to achieve a "high"), the pH-raising agent raises the pH of the surrounding liquid to a level sufficient to inhibit the release of active ingredient from the first portion. In some embodiments, the pH level that inhibits the release of active ingredient from the first portion is at least 3.5, more preferably at least 5, even more preferably at least 6, and most preferably at least 7.

In some embodiments, when a number of unit dosage forms, preferably at least three, more preferably at least four and most preferably at least five are administered concurrently or within a short time period, such as within one hour, preferably 30 minutes, more preferably 15 minutes, and most preferably within 5 minutes, the release of the active ingredient from the first portion is inhibited. In some embodiments, when a number of unit dosage forms, preferably at least three, more preferably at least four, and most preferably at least five, are placed in a container of liquid, the release of the active ingredient is inhibited. The release of the active ingredient from the first portion is considered to be inhibited, for example, if the amount and/or rate of release of active ingredient is lowered.

In some embodiments, when a subject attempts to abuse the active ingredient and achieve a "high" by taking a higher than recommended or prescribed number of unit dosage forms concurrently or within a short time period, the amount of active ingredient released from the first portion may be reduced by at least about 10%, preferably at least 25%, more preferably at least 50%, and most preferably at least 75%. In some embodiments, the oral pharmaceutical composition is configured such that when two or more unit dosage forms are administered to a subject with a time period of less one hour, the amount of active ingredient released from the two or more unit dosage forms is less than the total amount of active ingredient present in the two or more unit dosage forms. In some preferred embodiments, the use of two or more unit dosage forms concurrently or within a short time period may decrease the amount of active ingredient released from the first portion by at least about 50%, and the use of five or more unit dosage forms concurrently or within a short time period may decrease the amount of active ingredient released from the first portion by at least about 90%.

In some embodiments, the oral pharmaceutical composition is configured such that when a greater than the recommended or prescribed amount of unit dosages forms is ingested by a subject, less than the total amount of active ingredient present in the dosage forms is released. In some preferred embodiments, the amount of active ingredient released from the first portion is decreased by at least about 50%, preferably by at least about 60%, more preferably by at least 75%, and most preferably by at least about 90%.

In some embodiments, if a higher than recommended or prescribed number of unit dosage forms is administered or ingested by a subject, the rate of release of the active ingredient from the first portion may be reduced by at least about 10%, preferably at least 25%, more preferably at least 50%, and most preferably at least 75%. In some preferred embodiments, the use of two or more unit dosage forms concurrently or within a short time period may decrease the rate of release of active ingredient from the first portion is reduced by at least about 50%, and the use of five or more unit dosage forms concurrently or within a short time period may reduce the rate of release of active ingredient from the first portion by at least about 90%. In some embodiments, improper use of the pharmaceutical composition may result in an almost 100% reduction in the amount and/or rate of release of active ingredient, and no amount of active ingredient is released from the first portion.

In some embodiments wherein the pH-dependent component comprises a coating or layer which covers or surrounds the part of the first portion which comprises an active component, the release of the active ingredient may be affected by a reduction of the dissolution of the coating or layer. For example, at a certain pH, for example, at normal gastric pH, the coating or layer surrounding the part of the first portion comprising the active ingredient may dissolve substantially and then the total amount of active ingredient is released from the first portion. However, at another pH, for example, above pH 5, the dissolution of the coating or layer may be reduced, preferably significantly, and/or the coating or layer remain partially or substantially intact, and the total amount of the active ingredient may not release from the first portion. In some embodiments wherein the pH-dependent component forms a matrix in which the active ingredient is distributed, a similar effect may be achieved. For example, at a certain pH, for example, at normal gastric pH, the matrix may release the total amount of active ingredient from the first portion. However, at another pH, for example, above pH 5, the matrix may remain substantially intact or otherwise not release the total amount of the active ingredient from the first portion.

In preferred embodiments, the pharmaceutical composition is formulated for immediate release. The term "immediate release" is used to refer to a composition which is formulated to release at least 80% of an active ingredient after 4 hours, more preferably after 2 hours, and most preferably after 1 hour after administration.

The pharmaceutical composition of the present invention may also further comprise one or more pharmaceutically acceptable excipients including, but are not limited to, the following: plasticizers, anti-adhesives, fillers/diluents/binders, disintegrants, glidants and lubricants, surfactants, colorants, flavoring agents, pH adjusting agents, solubilizing agents, wetting agents, solvent resistant agents and buffering agents. Other suitable pharmaceutically acceptable excipients are described in *Remington: The Science and Practice of Pharmacy*, Lippincott Williams and Wilkins, Baltimore, Md. (1995), incorporated herein by reference.

Examples of plasticizers include, but are not limited to, triacetin, acetylated monoglyceride, olive oil, acetyl tributyl citrate, acetyl triethyl citrate, glycerin, sorbitol, polyethylene glycol, and polypropyleneglycol.

Examples of anti-adhesives include, but are not limited to, metallic stearates, microcrystalline cellulose, calcium phosphate, AEROSIL® 200, and talc. Those of ordinary skill in the art would understand the need for and applicability of such other components to overcome manufacturing, shelf-life or release profile issues.

Examples of fillers/diluents/binders include, but are not limited to, sucrose, sorbitol, mannitol, various grades of lactose, various grades of microcrystalline cellulose, dextrins, maltodextrins, starches or modified starches, sodium phosphate, calcium phosphate, calcium carbonate, gelatin, polyvinylpyrrolidone, and sodium carboxymethylcellulose.

Examples of disintegrants include, but are not limited to, cellulose derivatives, including microcrystalline cellulose, low-substituted hydroxypropyl cellulose, croscarmellose sodium, alginic acid, insoluble polyvinlypyrrolidone, and sodium carboxymethyl starch.

Examples of glidants and lubricants may be incorporated such as stearic acid, metallic stearates, talc, waxes, and glycerides with high melting temperatures, colloidal silica, sodium stearyl fumarate, polyethyleneglycols, and alkyl sulphates.

Examples of surfactants include, but are not limited to, non-ionic surfactants (such as various grades of polysorbate); anionic surfactants (such as docusate sodium and sodium lauryl sulfate), and cationic surfactants (such as benzalkonium chloride). An example of an amphoteric surfactant is 1,2-diacyl-L-phosphatidylcholine.

Other appropriate pharmaceutically acceptable excipients may include colorants, flavoring agents, pH adjusting agents, solubilizing agents, wetting agents, solvent resistant agents and buffering agents.

The present invention also provides methods of making the pharmaceutical composition of the present invention, comprising forming: (1) a first portion comprising: an active ingredient and a pH-dependent component, and (2) a second portion comprising a pH-raising agent. The first portion and second portion may be formed by any methods known in the art. In embodiments wherein the composition comprises a tablet dosage form, the tablet may be formed by any methods, such as those described in *Pharmaceutical Dosage Forms: Tablets, Third Edition*, Informa Healthcare, New York, N.Y. (2010), incorporated herein by reference. In some embodiments wherein the first portion and second portion together form a layered tablet, such as a bilayer or multilayer tablet, layers may be in powder form, and the layers may be compressed together using a tablet press.

The present invention also provides methods of preventing, treating, or reducing the symptoms associated with a condition, comprising administering to a subject in need thereof the pharmaceutical composition of the present invention. In some embodiments, the condition is a disease, disorder, illness, medical state, syndrome, or morbidity which would be improved, alleviated, treated, cured, or ameliorated by the administration of active ingredient.

EXAMPLES

Example 1

A tablet dosage form comprising a core containing an active ingredient and a pH-dependent polymer, and a coating comprising an alkalinizing agent is formulated. Three tablets are placed in 500 mL of Simulated Gastric Fluid (SGF) and the liquid medium is subjected to paddles at 50 rpm, and the dissolution profile is determined. The alkalinizing agent increases the pH to inhibit the release of the active ingredient from the dosage form, and less than 25% of the total amount of active ingredient in the tablets is released in 60 minutes.

Example 2

A tablet dosage form comprising a core containing an active ingredient and a pH-dependent polymer is formulated. The tablet dosage form does not have a coating comprising an alkalinizing agent. Three tablets are placed in 500 mL of Simulated Gastric Fluid (SGF) and the liquid medium is subjected to paddles at 50 rpm, and the dissolution profile is determined. More than 60% of the total amount of active ingredient in the tablets is released in 60 minutes.

Example 3

| | FORMULATION 1 | |
|---|---|---|
| Item | Ingredient | mg/tab |
| FIRST PORTION - ACTIVE TABLET COATED WITH pH COATING | | |
| Active Core Tablet | | |
| 1 | Oxycodone HCl | 15.0 |
| 2 | Avicel PH 102 | 69.5 |
| 3 | Aerosil 200 | 0.5 |
| 4 | Corn Starch | 14.0 |
| 5 | Mag Stearate | 1.0 |
| | Weight of Core Tablet | 100.0 |
| | Seal Coating onto active core tablet | |
| 6 | Methocel E6 Premium | 5.0 |
| 7 | Purified Water | Qs |
| | Weight of Seal coated tablet | 105.0 |
| | pH Coating onto Seal Coated Tablets | |
| 8 | Eudragit E-100 | 10.0 |
| 9 | Ethocel 45 | 3.0 |
| 10 | DBS | 1.5 |
| 11 | Mag Stearate | 3.5 |
| 12 | Ethanol | Qs |
| | Weight of the pH coated active tablets | 123.0 |
| SECOND PORTION - pH RAISING COMPONENT GRANULATION | | |
| 12 | Calcium Carbonate | 400.0 |
| 13 | Avicel PH 102 | 100.0 |
| 14 | Povidone K30 | 4.0 |
| 15 | Purified Water | QS |
| 16 | Magnesium Stearate | 2.0 |
| | Weight of the tablet | 506.0 |
| | FINISHED TABLET | |
| 17 | pH Coated Active Tablets | 123.0 |
| 18 | PH Raising Granulation | 506.0 |
| | Total Tablet Weight | 629.0 |

The above formulation may be made in the following manner: Procedure:

Step 1. Sieve Items 1,2,3 & 4 thru a 30-mesh screen.

Step 2. Blend step 1 for 10 minutes

Step 3. Sieve Item 5 thru 40-mesh screen and blend with step 2 for 3 minutes

Step 4. Compress to 100-mg weight and hardness of 7 kp.

Step 5. Apply Seal coating solution using perforated coating machine onto the active tablets from Step 4. After spraying the seal coat follow with the pH coating until a weight gain is achieved.

Step 6. Sieve items 12 and 13 through 20 mesh and blend for 10 minutes. Using a planetary mixer such as Hobart wet Granulate the powders by adding PVP solution (items 15 & 15) within 5 minutes. After granulation is complete dry using a Fluid bed dryer until LOD of NMT 2% moisture is achieved. Dry-Size the granules through a 20 mesh screen. Lubricate the milled granules with Item 16 for 5 minutes.

Step 7. Using a core coating tablet press, compress the coated tablet from the first portion and pH raising component granulation from the second portion into a finished tablet having 629 mg weight and hardness of 9-15 kp.

Example 4

The following is an exemplary formulation (Formulation 2)

| | FORMULATION 2 | |
|---|---|---|
| Item | Ingredient | mg/tab |
| FIRST PORTION - ACTIVE TABLET COATED WITH pH COATING Seal coated active powder | | |
| 1 | Oxycodone Hydrochloride | 30.0 |
| 2 | Methocel E6 Premium | 10.0 |
| 3 | Purified Water | Qs |
| | Weight of Seal coated active powder | 40.0 |
| pH Coating onto Seal Coated active powder | | |
| 4 | Eudragit E-100 | 10.0 |
| 5 | Ethocel 45 | 9.0 |
| 6 | DBS | 4.5 |
| 7 | Mag Stearate | 9.0 |
| 8 | Ethanol | Qs |
| | Weight of the pH coated active tablets | 72.5 |
| SECOND PORTION - pH RAISING COMPONENT GRANULATION | | |
| 9 | Calcium Carbonate | 300.0 |
| 10 | Aluminum hydroxide | 100.0 |
| 10 | Avicel PH 102 | 100.0 |
| 12 | Povidone K30 | 4.0 |
| 13 | Purified Water | QS |
| 14 | Magnesium Stearate | 2.0 |
| | Weight of the tablet | 506.0 |
| | Finished Tablet | |
| 15 | pH Coated Active powder | 72.5 |
| 16 | pH Raising Granulation | 506.0 |
| | Total Tablet Weight | 578.5 |

The above formulation may be made in the manner described in Example 3. Item #15 and Item #16 are core compressed into a single tablet using a core compression tablet press where ½ the weight of second portion is filled into the tablet die followed by coated active powder and finally remaining ½ weight of second portion into the same die so that the coated active powder will be covered by the second portion.

Example 5

| | Formulation 3 | |
|---|---|---|
| Item | Ingredient | mg/tab |
| FIRST PORTION - ACTIVE TABLET COATED WITH pH COATING Active Core Tablet | | |
| 1 | Morphine Sulfate | 30.0 |
| 2 | Avicel PH 102 | 54.5 |
| 3 | Aerosil 200 | 0.5 |
| 4 | Corn Starch | 14.0 |
| 5 | Mag Stearate | 1.0 |
| | Weight of Core Tablet | 100.0 |

| | Formulation 3 (continued) | |
|---|---|---|
| Item | Ingredient | mg/tab |
| Seal Coating onto active core tablet | | |
| 6 | Methocel E6 Premium | 5.0 |
| 7 | Purified Water | Qs |
| | Weight of Seal coated tablet | 105.0 |
| pH Coating onto Seal Coated Tablets | | |
| 8 | Eudragit E-100 | 10.0 |
| 9 | Ethocel 45 | 3.0 |
| 10 | DBS | 1.5 |
| 11 | Mag Stearate | 3.5 |
| 12 | Ethanol | Qs |
| | Weight of the pH coated active tablets | 123.0 |
| SECOND PORTION - pH RAISING COMPONENT GRANULATION | | |
| 12 | Sodium bicarbonate | 350.0 |
| 13 | Citric acid | 100.0 |
| 14 | Tartaric acid | 200.0 |
| 14 | Povidone K30 | 4.0 |
| 15 | Purified Water | QS |
| 16 | Magnesium Stearate | 2.0 |
| | Weight of the tablet | 656.0 |
| | Finished Tablet | |
| 17 | pH Coated Active Tablets | 123.0 |
| 18 | PH Raising Granulation | 656.0 |
| | Total Tablet Weight | 779.0 |

Example 6

| | Formulation 4 | |
|---|---|---|
| Item | Ingredient | mg/tab |
| FIRST PORTION - ACTIVE TABLET COATED WITH pH COATING active powder 1st granulation | | |
| 1 | Oxycodone Hydrochloride | 30.0 |
| 2 | Methocel E6 Premium | 10.0 |
| 3 | Magnesium stearate | 9.0 |
| 4 | Purified Water | Qs |
| | Weight of Seal coated active powder | 49.0 |
| Active powder 2nd (pH dependent) granulation | | |
| 5 | Eudragit E-100 | 10.0 |
| 6 | Ethocel 45 | 9.0 |
| 7 | Povidone k30 | 9.0 |
| 7 | Ethanol | Qs |
| | Weight of the pH coated active tablets | 77.0 |
| SECOND PORTION - pH RAISING COMPONENT GRANULATION | | |
| 9 | Calcium Carbonate | 400.0 |
| 10 | Avicel PH 102 | 100.0 |
| 12 | Povidone K30 | 4.0 |
| 13 | Purified Water | QS |
| 14 | Magnesium Stearate | 2.0 |
| | Weight of the tablet | 506.0 |
| | Finished Tablet | |
| 15 | Active powder 2nd granulation | 77.0 |
| 16 | pH Raising Granulation | 506.0 |
| | Total Tablet Weight | 583.0 |

The above formulation may be made in the manner described in Example 3. Active 1st and 2nd granulation are prepared using wet granulation technique where powders are dry mixed in a high shear granulator such as collette or low shear planetary mixer such as Hobart and then dried using a fluid bed dryer and dry-sized using milling equipment such as Fitz mill or oscillating granulator. Item #15 and Item #16 are blended together for 15 minutes and compressed into a single tablet using a tablet compression machine at 583 mg weight and hardness of 7-13 kp.

Example 7

The following describes an experiment to test the effect of a formulation of the present invention on AUC and Cmax. The study is a two-way crossover study involving administration of the following: (1) Formulation A: an immediate-release oxycodone formulation having a coating comprising a pH-raising agent, and (2) Formulation B: the formulation of Formulation A, without the coating comprising a pH-raising agent. Formulation A is a formulation of the present invention.

The AUC and Cmax are measured after each subject is administered: (1) one tablet, (2) two tablets, and (3) three tablets. Each subject is administered Formulation A and Formulation B.

The experiment shows that administration of Formulation B results in a dose proportional response, as the AUC and/or Cmax achieved after administration of two tablets of Formulation B was greater than (at least 25% greater than and sometimes about 100% greater than) the AUC and/or Cmax, respectively, achieved after administration of one tablet of Formulation B. The experiment also shows that the AUC and/or Cmax achieved after administration of three (3) tablets of Formulation B was greater than (at least 50% greater and sometimes about 200% greater than) the AUC and/or Cmax, respectively, achieved after administration of one tablet of Formulation B.

In contrast, the administration of Formulation A, a formulation of the present invention, did not result in a dose proportional response. Rather, administration of more than one tablet demonstrated a lower AUC and/or Cmax, compared to that achieved after administration of one tablet. For example, the AUC and/or Cmax achieved after administration of two tablets of Formulation A was lower than (at least about 10%, and sometimes about 25% lower) the AUC and/or Cmax, respectively, achieved after administration of one tablet of Formulation A. The experiment also shows that the AUC and/or Cmax achieved after administration of three (3) tablets of Formulation A was lower than (at least about 25% and sometimes about 50% lower than) the AUC and Cmax, respectively, achieved after administration of one tablet of Formulation A.

The results show that the administration of multiple tablets of the formulation of the present invention results in a lower AUC and/or Cmax compared to that achieved after administration of a smaller number of tablets.

What is claimed:

1. A method of treating pain in a subject in need thereof, comprising administering to the subject an immediate release oral pharmaceutical composition in unit dosage form comprising:
    (1) an inner first portion comprising: a first part comprising a core comprising an opioid selected from the group consisting of morphine, oxycodone, hydrocodone, oxymorphone, hydromorphone and codeine, or a pharmaceutically-acceptable salt thereof; and a seal coating, comprising a cellulose resin covering the core; and a second part comprising an acid-sensitive coating comprising a pH-dependent polymer selected from the group consisting of cationic polymers containing a dimethylaminoethyl ammonium group, wherein the acid-sensitive coating is coated on the seal coating of the inner first portion, and releases the opioid at a pH below 4, and wherein the second part substantially covers the first part; and
    (2) an outer second portion comprising a pH-raising agent of one or more alkaline compounds selected from the group consisting of sodium bicarbonate, potassium bicarbonate, calcium carbonate, aluminum hydroxide and magnesium hydroxide; and
    wherein the second portion substantially covers the first portion; and wherein when two or more unit dosage forms of the oral pharmaceutical composition are administered to a subject within a time period of less than one hour, the amount and/or rate of the opioid released from the first portion is at least about 10% less than the amount and/or rate of the opioid released from the first portion when one unit dosage form is administered.

2. The method of claim 1, wherein the unit dosage form comprises a tablet.

3. The method of claim 1, wherein the alkaline compound is present in an amount of about 50 mg to 2,500 mg.

4. The method of claim 1, wherein the alkaline compound is present in an amount of about 100 mg to 2,000 mg.

5. The method of claim 1, wherein the alkaline compound is present in an amount of about 250 mg to 1,500 mg.

6. The method of claim 1, wherein the opioid is selected from the group consisting of oxycodone and morphine, or a mixture thereof or a pharmaceutically acceptable salt thereof.

7. The method of claim 1, wherein when two or more unit dosage forms of said oral composition are administered to a subject within a time period of less than one hour, the amount and/or rate of said opioid released from the first portion is at least about 25% less than the amount and/or rate released from the first portion when one unit dosage form is administered.

8. The method of claim 7, wherein when two or more unit dosage forms of said oral composition are administered to a subject within a time period of less than one hour, the amount and/or rate of said opioid released from the first portion is at least about 50% less than the amount and/or rate released from the first portion when one unit dosage form is administered.

9. The method of claim 8, wherein when two or more unit dosage forms of said oral composition are administered to a subject within a time period of less than one hour, the amount and/or rate of said opioid released from the first portion is at least about 75% less than the amount and/or rate released from the first portion when one unit dosage form is administered.

10. The method of claim 1, wherein the acid-sensitive coating releases the opioid at a pH below 3.

11. The method of claim 1, wherein the alkaline compound is calcium carbonate or sodium bicarbonate.

12. The method of claim 1, which oral composition further comprises glidants, lubricants, surfactants, colorants, flavoring agents, and wetting agents.

13. The method of claim 12, wherein said surfactants in said oral comprise non-ionic, anionic, cationic and ampho-teric surfactants.

14. The method of claim 1, wherein said opioid in said oral composition comprises about 3-400 mg of oxycodone or a pharmaceutically acceptable salt thereof, and about 5-800 mg of morphine or a pharmaceutically acceptable salt thereof per unit dosage form.

\* \* \* \* \*